US 6,613,948 B1

(12) United States Patent
Neuner et al.

(10) Patent No.: US 6,613,948 B1
(45) Date of Patent: Sep. 2, 2003

(54) PROCESS FOR THE PREPARATION OF 2,3,4,5-TETRAFLUOROBENZENE DERIVATIVES

(75) Inventors: Otto Neuner, Bergisch Gladbach (DE); Norbert Lui, Köln (DE); Dietmar Bielefeldt, Ratingen (DE); Michael Holzbrecher, Engelskirchen (DE)

(73) Assignee: Bayer AG (DE)

( * ) Notice: Subject to any disclaimer, the term of this patent is extended or adjusted under 35 U.S.C. 154(b) by 505 days.

(21) Appl. No.: 09/152,595

(22) Filed: Sep. 14, 1998

(30) Foreign Application Priority Data

Sep. 16, 1997 (DE) .......................... 197 40 632

(51) Int. Cl.⁷ .......................... C07C 22/00; C07C 25/13
(52) U.S. Cl. ........................ 570/143; 570/144
(58) Field of Search ................. 570/143, 144; 558/425; 562/549

(56) References Cited

U.S. PATENT DOCUMENTS

| 4,937,396 A | * | 6/1990 | Pews et al. ................. 570/144 |
| 5,565,614 A | | 10/1996 | Klauke et al. .............. 562/849 |
| 5,599,980 A | | 2/1997 | Marhold et al. ............ 562/840 |

FOREIGN PATENT DOCUMENTS

| CA | 1242742 | 4/1988 |
| DE | 3420796 A1 | 5/1985 |
| EP | 0607 824 A2 | 7/1994 |

OTHER PUBLICATIONS

XP002165316, Chemical Abstracts Service, titled "Manufacture of 2,3,4,5–tetra–fluorobenzoic acid", vol. 117, dated Aug. 17, 1992, 1 page.

XP–002165317, "Manufacture of 2,3,4,5–tetra–fluorobenzoic acid", Casreact Acession No. 117:69574, dated Feb. 18, 1992, 2 pages.

Copy of PCT Search Report for corresponding patent application WP 98 11 6713, dated Sep. 12, 2001, 2 pages.

* cited by examiner

Primary Examiner—Samuel Barts
Assistant Examiner—Elvis O. Price
(74) Attorney, Agent, or Firm—Brinks Hofer Gilson & Lione; Gregory H. Zayia

(57) ABSTRACT 2,3,4,5-tetrafluorobenzene derivatives can be obtained in a particularly advantageous manner by reacting the corresponding chlorobenzene or (chloro, fluoro)-benzene derivatives with a fluorinating agent in the presence of a solvent and a catalyst at elevated temperature, which comprises carrying out the reaction initially under temperature and pressure conditions such that the respective 2,3,4,5-tetrafluoro-benzene derivative continuously distills off through a column, and subsequently setting temperature and pressure conditions such that residual fractions of the 2,3,4,5-tetrafluorobenzene derivative distill off with the corresponding 2,3,4-trifluoro-5-chloro compound.

9 Claims, No Drawings

PROCESS FOR THE PREPARATION OF 2,3,4,5-TETRAFLUOROBENZENE DERIVATIVES

The present invention relates to an improved process for the preparation of 2,3,4,5-tetrafluorobenzene derivatives from 2,3,4,5-tetrachloro- and/or 2,3,4.5-tetra-(chloro, fluoro)-benzene derivatives by chlorine/fluorine exchange.

DE-A 3 420 796 describes a process for the preparation of 2,3,4,5-tetrafluorobenzene derivatives, in which 2,3,4,5-tetrachlorobenzene derivatives are reacted with potassium fluoride in a solvent at elevated temperature. Using 2,3,4,5-tetrachlorobenzoyl fluoride as starting material and continuously distilling off the mixture of the fluorination products at from 800 to 500 mbar produces, after fractional distillation of the mixture of the fluorination products, the desired 2,3,4,5-tetrafluorobenzoyl fluoride in a yield of only 10% of theory, while significantly more undesired fluorination products are obtained, namely 2,3,4-trifluoro-5-chlorobenzoyl fluoride in a yield of 43% of theory and 2,4-difluoro-3,5-dichlorobenzoyl fluoride in a yield of 14% of theory (see Example 2 in DE-A). If 2,3,4,5-tetrachlorobenzonitrile is used as starting material and the fluorination mixture is subjected to fractional distillation, the ratios are obviously similar, although no information concerning the amounts of the tetrafluoro-, tetrafluorochloro- and difluorodichlorobenzonitriles obtained is given (see Example 5 in DE-A).

EP-A 607 824 describes a process for the preparation of 2,3,4,5-tetrafluoro-benzotrifluoride by reacting tetrachlorobenzotrifluoride with potassium fluoride. Using pure 2,3,4,5-tetrachlorobenzotrifluoride as starting material and working up the reaction mixture by distillation gives a crude distillate which comprises the 2,3,4,5-tetrafluorobenizotifluoride in an amount of from 54 to 62% of theory (see Example Group A. 4th example, parts a), b), c) and e) in EP-A). If mixtures of 2,3,4,5-tetrachloro- and 2,3,4-trifluoro-5-chlorobenzotrilfluoide are used as starting materials, the content of 2,3,4,5-tetrafluorobenizotifluoride in the crude distillate drops to 51% of theory (see Example group A. 4th example, part d) in EP-A). For recovery rates (i.e. the sum of the yields of 2,3,4,5-tetrafluoro- and 2,3,4-trifluoro-5-chlorobenzotrilfluoide) of about 90%, the yields of 2,3,4,5-tetrafluoro-benzo-trifluoride are only from 50 to 55% of theory, but the yields of 2,3,4-trifluoro-5-chlorobenzotrifluoride are from 34 to 38% of theory (see Example Group A, 4th Example, parts d) and e) in EP-A). This means that in order to prepare 2,3,4,5-tetrafluorobenzotrifluoride, from almost 40 to 50% of the recovery rate of 2,3,4-trifluoro-5-chlorobenzotrifluoride must be recycled, and thus the expenditure is high and the space-time yield is low.

There therefore continues to be a need for a process for the preparation of 2,3,4,5-tetrafluorobenzene derivatives in which the desired products are obtained in good yields and selectivities.

We have now found a process for the preparation of tetrafluorobenzene derivatives of the formula (I)

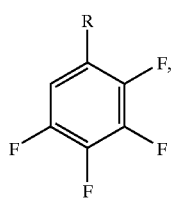

(I)

in which
  R is $CF_3$, CN or COF.
  by reacting a chlorobenzene derivative of the formula

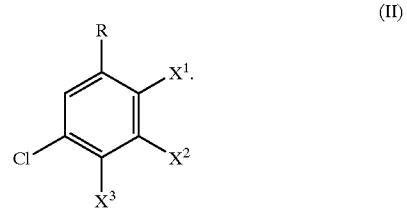

(II)

in which
  R is as defined for formula (I), and
  $X^1$, $X^2$ and $X^3$ independently of one another are each F or Cl,
with a fluorinating agent in the presence of a solvent and a catalyst at elevated temperature, which comprises carrying out the reaction initially under temperature and pressure conditions such that the respective compound of the formula (I) is continuously distilled off through a column, and subsequently setting the temperature and pressure conditions such that remaining fractions of the compound of the formula (I) are distilled off together with the corresponding 2,3,4-trifluoro-5-chloro compound.

The novel process preferably uses compounds of the formula (II) in which $X^1$, $X^2$ and $X^3$ are chlorine or those compounds of the formula (II) in a mixture with compounds of the formula (II) in which $X^1$, $X^2$ and $X^3$ are fluorine.

Examples of suitable fluorinating agents are alkali metal fluorides, such as sodium fluoride, potassium fluoride, cesium fluoride and mixtures of said fluorides. Preference is given to potassium fluoride, particularly in spray-dried form.

Per equivalent of chlorine atoms to be replaced, it is possible to use, for example, at least 1 equivalent of fluorinatin agent. This amount is preferably from 1.1 to 1.5 equivalents of fluorinating agent. Larger amounts do not cause any problems, but are uneconomical.

Suitable solvents are dipolar aprotic solvents, such as tetramethylene sulfone (sulfolane). N-methylpyrrolidone, dimethyl sulfoxide, dimethylformanide, dimethylacetamide, diglyme, tetraglyme and 1,3-dimethyliymiidalzolidinonc. Preference is given to tetramethylene Sulfone (sulfolane). The solvent can be used, for example, in an amount of from 1 kg to 10 kg, based on 1 kg of fluorinating reagent. Larger amounts do not cause any problems, but are uneconomical.

Examples of suitable catalysts are phase transfer catalysts, such as quaternary ammonium salts, pyridinium salts, quaternary phosphonium salts and crown ethers. Individual examples which may be mentioned are: tetramethylammonium chloride, tetrabutylammonium bromide, N-neopentyl-4-(N',N'-dimethylamino)-pyridinium chloride, tetrabutylphosphonium bromide, tetraphenylphosphonium bromide and 18-crown 6. Preference is given to tetraphenylphosphonium bromide. Based on the starting compound(s) of the formula (II), from 1 to 50% by weight, preferably from 4 to 15% by weight, of catalyst, based on the feed material, may, for example, be used.

The reaction temperature can be, for example, in the range from 160 to 250° C., it is preferably in the range from 190 to 230° C.

It is an essential feature of the present invention that, for a given reaction temperature, the pressure is initially set such that the respective compound of the formula (I) is continuously distilled off. The optimum pressure in each individual case can be easily determined by routine preliminary tests. It has been found that pressures in the range from, for example, 1.3 to 6 bar, frequently in the range from 2 to 4 bar, are generally required for this purpose.

The compound of the formula (I) produced during the reaction is generally the lowest boiling component of the reaction mixture. The pressure is initially chosen such that practically only the compound of the formula (I) formed distills off and practically none of the higher boiling constituents of the reaction mixture. When tetrachlorobenzotrifluoride and a reaction temperature of from 200 to 220° C. are used, pressures in the range from 2.1 to 2.3 bar, for example, have proven successful.

After the reaction has ended, virtually no more of compound of the formula (I) passes over and the pressure drops. From this moment, pressure and temperature conditions are set according to the invention such that fractions of the compound of the formula (I) still present in the reaction mixture distill of together with the corresponding 2,3,4-trifluoro-5-chloro compound. To achieve this, it is generally sufficient to only lower the pressure, for example, down to a rank from 50 to 200 mbar. It is preferable to collect the first fraction (=virtually pure compound of the formula (I)) and the second fraction (=mixture of the compound of the formula (I) and the corresponding 2,3,4-trifluoro-5-chloro compound) separately from one another.

The whole of the second fraction, or, in an advantageous manner, only the partially fluorinated compounds present therein after they have been removed, is/are added to the next batch in order to carry out the novel reaction to give the compound of the formula (I).

Compounds of the formula (I) are obtained in the novel way in significantly better yields and selectivities than previously. In the case of the novel process, the yields of compounds of the formula (I) are, for example, in the range from 65 to 75% of theory and the yields of corresponding 2,3,4-trifluoro-5-chloro compounds are, for example, in the range from only 12 to 18% of theory. This means that, in a straight pass, significantly more of the product of the formula (I) and significantly less of the corresponding 2,3,4-trifluoro-5-chloro compound are obtained in the process according to the invention than according to EP-A-607 824. A particular consequence of this is that, according to the invention, only approximately half the amount of 2,3,4-trifluoro-5-chloro compounds has to be recycled. The desired compounds of the formula (I) can thus be prepared at significantly lower cost (for example on solvents, fluorinating agents, catalysts, distillation expenses etc.) and with significantly higher space-time yields than previously.

EXAMPLES

Example 1

A 5 l autoclave made of stainless steel fitted with a stirrer, column, reflux divider, condenser with pressure relief valve and 1,000 ml exchangeable receiver was charged with a mixture, predried by distillation, of 2,750 g of sulfolane (pure) and 1,000 g of potassium fluoride (anhydrous); 50 g of tetraphenylphosphonium bromide and 1,050 g of 2,3,4,5-tetrachlorobenzotrifluoride (distilled) were introduced, and after sealing the autoclave pressure-tight, the mixture was heated to 210° C. with stirring. The incipient formation of 2,3,4,5-tetrafluorobenzotrifluoride and 2,3,4-trifluoro-5-chlorobenzotrifluoride caused the overall pressure in the equipment to increase gradually up to 2.2 bar. As soon as the head temperature had increased to 130° C. in the column under the reaction conditions (total pressure: 2.2 bar and internal temperature: 210° C.), distillate was drawn off into the receiver at a reflux ratio of take-off: reflux=1:10. Whilst the distillate was being drawn off, the reaction and distillation conditions were kept constant. Towards the end of the reaction, the overall pressure dropped and distillation of the 2,3,4,5-tetrafluorobenzotrifluoride subsided noticeably. After the reaction had ended and the overall pressure had dropped, a mixture of 2,3,4,5-tetrafluoro- and 2,3,4-trifluoro-5-chlorobenzo-trifluoride was removed by decompression to 1 bar. By subsequently setting a pressure of from 50 to 100 mbar, the volatile fractions still present in the sulfolane were distilled into the emptied receiver until the boiling point of sulfolane was reached. In a total yield of 85% of theory, based on 2,3,4,5-tetrachloro-benzotrifluoride used. 565 g (=70% of theory) of 2,3,4,5-tetrafluorobenzotrifluoride and 130 g (15% of theory) of 2,3,4-trifluoro-5-chlorobenzotrifluoride were obtained. The partially fluorinated benzotrifluoride was added to the next batch for the preparation of 2,3,4,5-tetrafluorobenzotrifluoride.

Example 2

A 5 l autoclave was charged with a mixture of 2,700 g of sulfolane (pure) and 980 g of potassium fluoride (anhydrous); 55 g of tetraphenylphosphonium bromide and a mixture of 1,000 g of 2,3,4,5-tetrachlorobenzotrifluoride and 130 g of 2,3,4-trifluoro-5-benzotrifluoride were added, the procedure being otherwise as described in Example 1. All of the volatile fractions were distilled off by fractional distillation to leave, in a yield of 86% of theory, based on 2,3,4,5-tetrachlorobenzotrifluoride and 2,3,4-trifluoro-5-chlorobenzotrifluoride used, 635 g (=71.5% of theory) of 2,3,4,5-tetrafluorobenzotrifluoride and 140 g (=14.6% of theory) of 2,3,4-trifluoro-5-chlorobenzotrifluoride.

Example 3

A 130 l autoclave made of 1.4571 fitted with paddle stirrer, column, reflux divider, condenser with pressure relief valve and exchangeable receiver was charged with 61 kg of sulfolane (pure) and 20 kg of potassium fluoride (anhydrous), and water was removed from the mixture by distilling off 10 kg of sulfolane. The solution of 1 kg of tetraphenylphosphonium bromide in 6 kg of sulfolane (anhydrous) was then firstly pumped into the suspension, which had a temperature of approximately 180° C., and, after sealing the autoclave pressure-tight and further heating to 210° C. 19.5 kg of 2,3,4,5-tetrachlorobenzotrifluoride (distilled) were pumped in.

With further stirring at from 210° C. to 220° C. the pressure rose gradually up to about 2.2 bar.

The mixture was then further processed as described in Example 1.

The batch was worked up to give, in an overall yield of 91.66%, based on 2,3,4,5-tetrachlorobenzotrifluoride (distilled). 11.2 kg of 2,3,4,5-tetrafluorobenzotrifluoride (=74.89% of theory) and 2.7 k of 2,3,4-trifluoro-5-chlorobenzotrifluoride (=16.8% of theory).

What is claimed is:
1. A process for the preparation of tetrafluorobenzene derivatives of the formula (I):

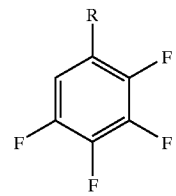

in which R is CF$_3$, CN or COF, comprising:
reacting a chlorobenzyene derivative of the formula (II):

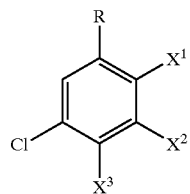

in which R is as defined for Formula (I) and X$^1$, X$^2$ and X$^3$, independently of one another, are each F or Cl, with potassium fluoride in the presence of a solvent and a catalyst under an initial pressure of from 1.3 to 6 bar and at an initial temperature of from 160 to 230° C., such that the compound (I) is continuously distilled off through a column, and subsequently setting the temperature and pressure conditions such that remaining fractions of the compound (I) distill off together with 2,3,4-trifluoro-5-chloro compound.

2. A process as claimed in claim 1, wherein the initial reaction temperature is in the range from 190 to 230° C.

3. A process as claimed in claim 1, wherein, for a given reaction temperature, the pressure is initially set such that the respective compound of the formula (I) is continuously distilled off.

4. A process as claimed in claim 1, wherein the initial pressure is at from 2 to 4 bar.

5. A process as claimed in claim 1, wherein, when virtually no more of compound of the formula (I) passes over, the pressure is reduced to from 50 to 200 mbar.

6. A process as claimed in claim 1, wherein, in formula (II) X$^1$, X$^2$ and X$^3$ are chlorine.

7. A process as claimed in claim 1, wherein mixtures of compounds of the formula (II) in which X$^1$, X$^2$ and X$^3$ are chlorine, with compounds of the formula (II) in which X$^1$, X$^2$ and X3 are fluorine are used.

8. A process as claimed in claim 1, wherein the solvent used is a dipolar aprotic solvent.

9. A process as claimed in claim 1, wherein the catalyst used is a phase transfer catalyst.

* * * * *